(12) United States Patent
Lechot

(10) Patent No.: US 6,506,000 B2
(45) Date of Patent: Jan. 14, 2003

(54) MILLING CUTTER AND CUTTER HOLDER

(75) Inventor: André Lechot, Orvin (CH)

(73) Assignee: PreciMed S.A., Orvin (CH)

( * ) Notice: Subject to any disclaimer, the term of this patent is extended or adjusted under 35 U.S.C. 154(b) by 27 days.

(21) Appl. No.: 09/735,829

(22) Filed: Dec. 13, 2000

(65) Prior Publication Data

US 2001/0006593 A1 Jul. 5, 2001

(30) Foreign Application Priority Data

Dec. 22, 1999 (CH) .............................................. 2351/99

(51) Int. Cl.⁷ ............................ B23C 5/20; B26D 1/12
(52) U.S. Cl. ................................... 407/35; 407/43
(58) Field of Search ........................... 407/42, 43, 50, 407/55, 58, 62, 64–65; 82/163–165, 170; 606/79–82, 167, 179, 180; 409/234

(56) References Cited

U.S. PATENT DOCUMENTS

| | | | | |
|---|---|---|---|---|
| 4,204,787 A | * | 5/1980 | McCray et al. | 407/49 |
| 4,586,855 A | * | 5/1986 | Rawle | 407/38 |
| 5,501,686 A | * | 3/1996 | Salyer | 606/79 |
| 6,264,647 B1 | * | 7/2001 | Lechot | 606/1 |

* cited by examiner

Primary Examiner—A. L. Wellington
Assistant Examiner—Brian Walsh
(74) Attorney, Agent, or Firm—Bugnion S.A.; John Moetteli

(57) ABSTRACT

The cutter holder (1) has, on the one hand, parallel fixed fingers (7) equipped with a groove (15) and, on the other hand, moving locking fingers (10) of which the end (16) is preferably conical. The milling cutter (6) has at least one flat annular part pierced, on the one hand, with fixing holes and, on the other hand, with locking holes which are slightly angularly offset with respect to the locking fingers in a direction which is the opposite to the direction of rotation of the cutter. Once the cutter has been fitted over the fixed fingers and engaged in the grooves (15), engaging the locking fingers in the locking holes has the effect of locking the cutter on the fixing fingers.

46 Claims, 2 Drawing Sheets

MILLING CUTTER AND CUTTER HOLDER

BACKGROUND OF THE INVENTION

The subject of the invention is a milling cutter and a cutter holder particularly, although not exclusively, for surgical use.

SUMMARY OF THE INVENTION

The object of the invention is to produce a quick fixing for a milling cutter, particularly for an essentially flat, disk-shaped cutter.

The milling cutter and the cutter holder, according to the invention, are ones wherein the cutter has a part of flat annular shape pierced with at least two fixing holes uniformly distributed on a circle and with at least one locking hole, and the cutter holder has, on the one hand, at least two parallel fixed fingers uniformly distributed on a circle of the same diameter as the circle passing through the fixing holes in the cutter, these fingers having a head of a diameter smaller than the diameter of the fixing holes, a groove under this head, of a height corresponding to the thickness of the annular part of the cutter, and, under the groove, a diameter larger than the diameter of the fixing holes and, on the other hand, at least one locking finger parallel to the fixed fingers and moveable parallel to the fixed fingers, this moving finger occupying, around the axis of the support, relative to the fixed fingers, the same position as the locking hole relative to the fixing holes but with an angular offset in a direction which is the opposite to the direction of rotation of the cutter, so that once the cutter has been engaged over the fixed fingers and engaged in the grooves, in the opposite direction to its direction of rotation, introducing the moving finger into the locking hole has the effect of locking the cutter in the grooves.

The locking finger may simply be cylindrical. In this case, to avoid the fixing exhibiting angular backlash, the fixing hole and the locking finger need to be made and positioned with great accuracy. This requirement can be dispensed with by using a locking finger the end of which is conical so that engagement of the conical end in this locking hole has the effect of pushing the cutter into the grooves.

The cutter preferably has three locking holes to which three conical-ended locking fingers on the cutter holder correspond.

This fixing mode can apply to any cutter which has a flat annular part, the central part possibly having the desired shape, for example hemispherical or conical.

According to one preferred embodiment of the invention, the fixed fingers are carried by a flange, while the locking fingers arc carried by an annular support constrained so as to slide axially on the cutter holder, passing through the flange and guided in this flange.

The annular support of the locking fingers is pushed by a spring so that when the annular support is released, the conical fingers automatically engage in the locking holes. The spring maintains the lateral thrust of the locking fingers on the cutter.

This milling cutter and cutter holder assembly is particularly intended for one-use surgical cutters.

BRIEF DESCRIPTION OF THE DRAWINGS

The appended drawing depicts, by way of example, one embodiment of the invention.

DESCRIPTION OF THE PREFERRED EMBODIMENT(S)

Figure 1:
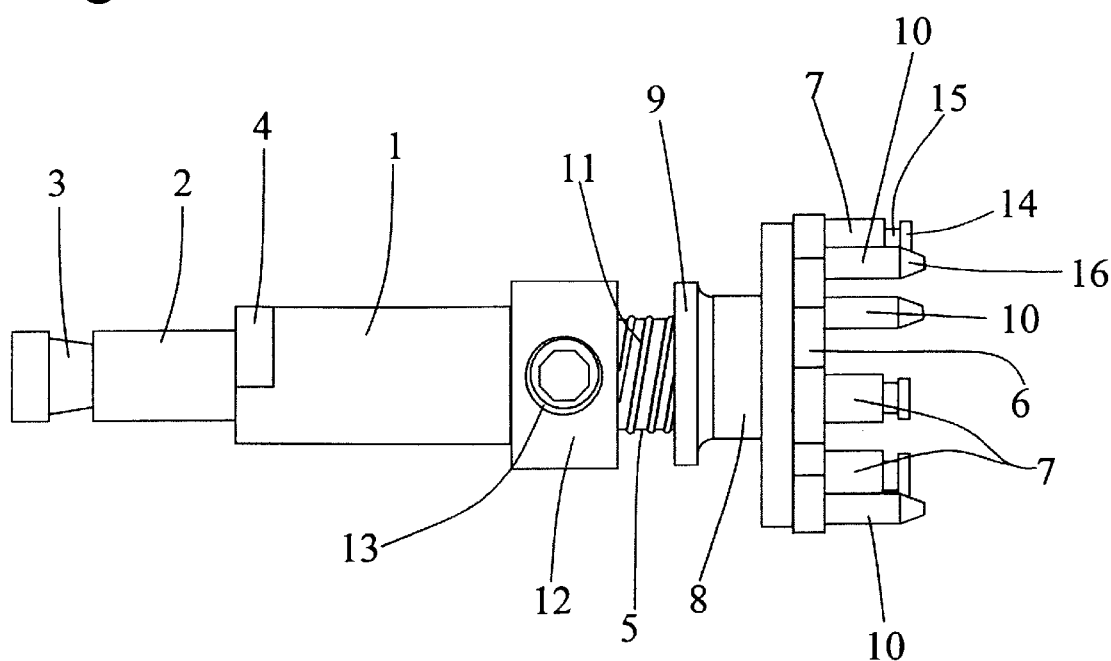
FIG. 1 is a side view of the cutter holder without the cutter.
Figure 2:
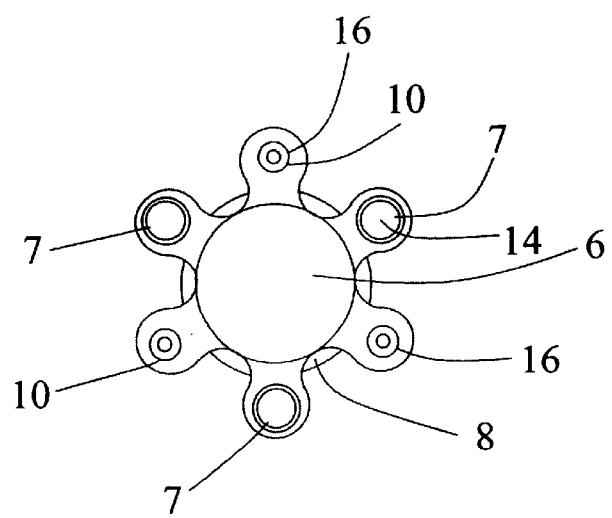
FIG. 2 is a front view of the cutter holder without the cutter.

The cutter holder comprises a cylindrical body 1 equipped with a shank 2 with an annular groove 3. The body 1 has two opposed flats 4. This part of the cutter holder is intended to be fixed axially and angularly in a rotational drive device.

At the front of the cylindrical body 1, the cutter holder has a part 5 of smaller diameter, to the end of which is fixed a flange 6 carrying three fixed fingers 7 which are parallel to the axis of the cutter holder and uniformly distributed on a circle centered on the axis of the cutter holder.

Mounted freely on the smaller-diameter part 5 is a ring 8 equipped with a collar 9 and carrying three fingers 10 parallel to the axis of the cutter holder and uniformly distributed on a circle, which, in the embodiment depicted, coincides with the circle passing through the fixed fingers 7. The ring 8 is pushed forward by a spring 11 working in compression between the ring 8 and a ring 12 fixed on the cylindrical body 1 by means of a screw 13. The fingers 10 pass through the flange 6 via holes guiding the locking fingers 10 and angularly positioning them relative to the fixed fingers 7. The flange 6 is notched between the fingers 7 and 10 to allow the passage of the chips detached by the cutter.

The fixed fingers 7 have a head 14 under which an annular groove 15 is formed. The diameter of the head 14 is smaller than the diameter of the body of the finger 7. The locking fingers 10 have a conical, or more precisely a frustoconical end 16.

Figure 3:
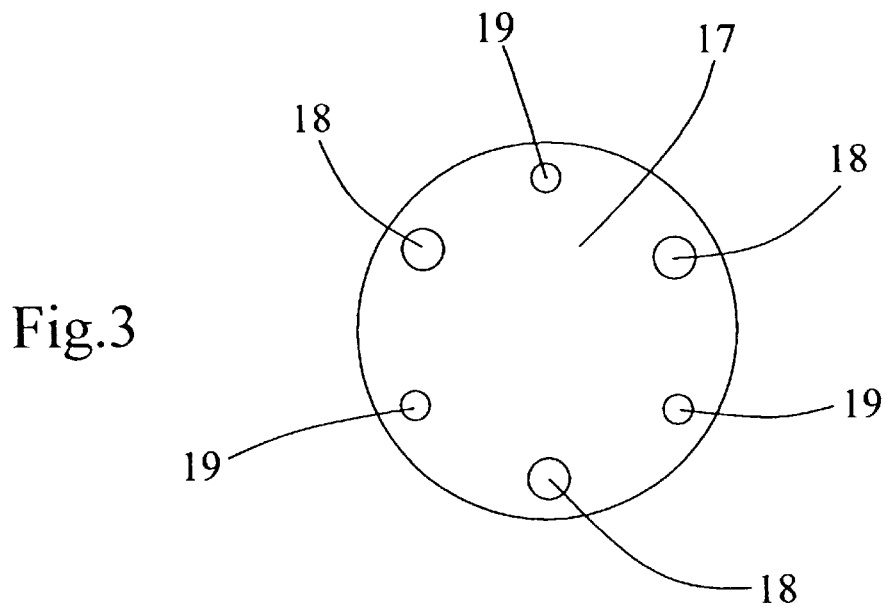
FIG. 3 depicts the cutter.

The miller cutter depicted diagrammatically in FIG. 3 in the form of a simple disk 17 has three fixing holes 18 uniformly distributed on a circle of a diameter equal to the diameter of the circle passing through the fixed fingers 7.

The diameter of the holes 18 is greater than the diameter of the heads 14 of the fingers 7 but smaller than the diameter of the body of the fingers 7 under the groove 15. The cutter 17 also has three locking holes 19 located, in the example depicted, on the same circle as the fixing holes 18 and also uniformly distributed on this circle. The diameter of the holes 19 is smaller than the diameter of the locking fingers and the locking fingers are slightly angularly offset with respect to the holes 19 in a direction which is preferably opposite direction to the direction in which the cutter holder rotates (an offset in either direction will function, however, a direction opposite to the direction of rotation is most stable).

Figure 4:
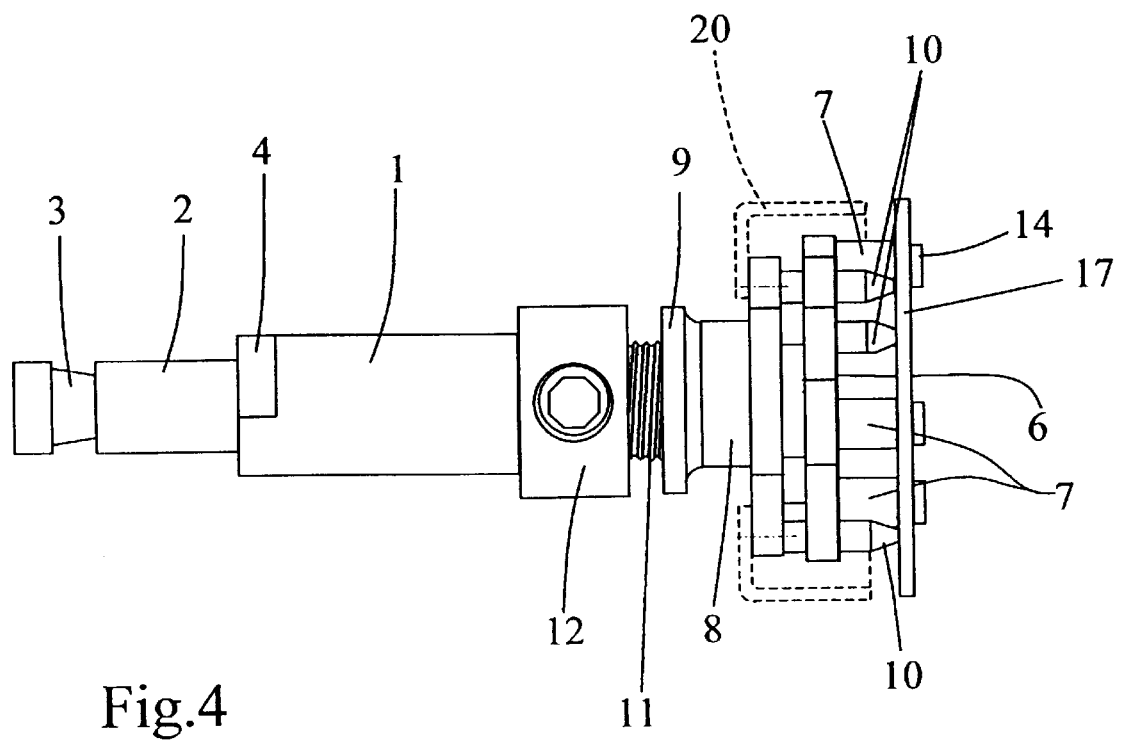
FIG. 4 depicts the cutter assembled with the cutter holder.

Referring now to FIG. 4, to fix the cutter holder, the ring 8 is drawn back via its collar 9, compressing the spring 11. The cutter is then placed on the cutter holder by introducing the heads 14 of the locking fingers 10 into the fixing holes 18, the diameter of which is appreciably larger than the diameter of the heads 14 so as to make the fit very easy. The cutter is then engaged in the grooves 15 by rotating the cutter slightly in the opposite direction to the direction of rotation of the cutter holder, then the ring 8 is released. The conical ends 16 of the fingers 7 then enter the holes 19 of the cutter, but as they are angularly offset with respect to the holes 19, they tend to recenter the holes 19 on the fingers 10 and therefore to drive the cutter in the opposite direction to its direction of rotation when at work. The cutter 17 is therefore pushed into the grooves 15 and thus locked without backlash in these grooves.

Shown in phantom is a bell housing 20 which surrounds the fingers in order to collect chips.

To remove the cutter, all that is required is for the ring 8 to be drawn back.

The cutter holder could be supplemented by a bell housing surrounding the fingers, which bell housing would allow the chips cut by the cutter to be collected.

In general, there will be three fixing holes and three fixing locking fingers to hold the cutter on firmly, but one single locking finger may prove sufficient. However, if the cutter has just one locking hole, it will be necessary for the cutter to be angularly positioned when it is put in place on the fixed fingers 7.

It is obvious that the locking fingers do not necessarily have to be on the same circle as the fixed fingers and, correspondingly, that the locking holes 19 do not necessarily have to be on the same circle as the fixing holes 18.

The groove 15 does not necessarily have to be circular but could be present simply on the opposite side to the direction of travel of the cutter driving the locking fingers.

Multiple variations and modifications are possible in the embodiments of the invention described here. Although certain illustrative embodiments of the invention have been shown and described here, a wide range of modifications, changes, and substitutions is contemplated in the foregoing disclosure. In some instances, some features of the present invention may be employed without a corresponding use of the other features. Accordingly, it is appropriate that the foregoing description be construed broadly and understood as being given by way of illustration and example only, the spirit and scope of the invention being limited only by the appended claims.

What is claimed:

1. A milling cutter and cutter holder, wherein the cutter (17) is a part of flat annular shape having at least two fixing holes (18) located in a pattern and having at least one locking hole (19), and wherein the cutter holder has at least two fixed fingers (7) axially parallel to a rotational axis of the cutter holder and located in a pattern, that matches the pattern of the fixing holes in the cutter so as to engage therein, these fingers having a head (14) of a maximum transverse dimension smaller than a minimum diameter of the fixing holes (18), a groove (15) under this head, of a width corresponding to the thickness of the annular part of the cutter, and, under the groove, a minimum transverse dimension larger than a maximum diameter of the fixing holes and, further, at least one locking finger (10) parallel to the fixed fingers (7) and constrained so as to move along an axis parallel to the fixed fingers, angularly offset an approximately identical amount as the fixing holes are from the locking holes on the cutter but with an angular shift preferably in a direction which is the opposite to the direction of rotation of the cutter, so that once the cutter has been engaged over the fixed fingers and engaged in the grooves, in the opposite direction to the direction of rotation of the cutter, introduction of the moving finger into the locking hole locks the cutter in the grooves.

2. The milling cutter and cutter holder as claimed in claim 1, wherein the locking finger (10) has a conical end (16).

3. The milling cutter and cutter holder as claimed in claim 2, wherein the locking finger (10) is cylindrical adjacent its conical end (16) and has a diameter larger than the diameter of the locking hole (19).

4. The milling cutter and cutter holder as claimed in claim 1, wherein the locking finger (10) is mounted on a component (8) mounted to slide on the cutter holder and biased into a locking position by a spring (11).

5. The milling cutter and cutter holder as claimed in claim 2, wherein the locking finger (10) is mounted on a component (8) constrained to axially slide on the cutter holder and is biased into its locking position by a spring (11).

6. The milling cutter and cutter holder as claimed in claim 3, wherein the locking finger (10) is mounted on a component (8) mounted to slide on the cutter holder and pushed into its locking position by a spring (11).

7. The milling cutter and cutter holder as claimed in claim 4, wherein the fixed fingers (7) are carried by a flange and the locking finger (10) is guided through this flange.

8. The milling cutter and cutter holder as claimed in claim 5, wherein the fixed fingers (7) are carried by a flange and the locking finger (10) is guided through this flange.

9. The milling cutter and cutter holder as claimed in claim 6, wherein the fixed fingers (7) are carried by a flange and the locking finger (10) is guided through this flange.

10. The milling cutter and cutter holder as claimed in claim 7, wherein the cutter (17) has three locking holes (19) uniformly distributed about the axis of the cutter holder and the cutter holder has three locking fingers (10) uniformly distributed about the axis of the cutter holder.

11. The milling cutter and cutter holder as claimed in claim 10, wherein the holes and the fingers are radially equidistant from the rotational axis.

12. The milling cutter and cutter holder as claimed in claim 1, wherein the cutter holder is equipped with a bell housing surrounding the fingers to collect the chips.

13. The milling cutter and cutter holder as claimed in claim 2, wherein the cutter holder is equipped with a bell housing surrounding the fingers to collect the chips.

14. The milling cutter and cutter holder as claimed in claim 3, wherein the cutter holder is equipped with a bell housing surrounding the fingers to collect the chips.

15. The milling cutter and cutter holder as claimed in claim 4, wherein the cutter holder is equipped with a bell housing surrounding the fingers to collect the chips.

16. The milling cutter and cutter holder as claimed in claim 5, wherein the cutter holder is equipped with a bell housing surrounding the fingers to collect the chips.

17. The milling cutter and cutter holder as claimed in claim 6, wherein the cutter holder is equipped with a bell housing surrounding the fingers to collect the chips.

18. The milling cutter and cutter holder as claimed in claim 7, wherein the cutter holder is equipped with a bell housing surrounding the fingers to collect the chips.

19. The milling cutter and cutter holder as claimed in claim 8, wherein the cutter holder is equipped with a bell housing surrounding the fingers to collect the chips.

20. The milling cutter and cutter holder as claimed in claim 9, wherein the cutter holder is equipped with a bell housing surrounding the fingers to collect the chips.

21. The milling cutter and cutter holder as claimed in claim 10, wherein the cutter holder is equipped with a bell housing surrounding the fingers to collect the chips.

22. The milling cutter and cutter holder as claimed in claim 11, wherein the cutter holder is equipped with a bell housing surrounding the fingers to collect the chips.

23. A cutting device comprising:
   a milling cutter (17) with at least two fixing holes (18) and an at least one locking hole (19); and
   a holder with at least two axially fixed finger (7) having grooves (15), and at least one locking finger (10)

positioned to move in an axial direction relative to the at least two fixed fingers (7) and able to penetrate into the at least one locking hole, said relative axial motion and penetration cause the milling cutter (17) to rotationally engage the groove (15) in a locked manner.

24. A cutter holder adapted to securely hold a miffing cutter (17) of flat annular shape pierced with at least two fixing holes (18) uniformly distributed on a circle centered on a rotational axis and with at least one locking hole (19), the cutter holder having at least two fixed fingers (7) parallel to the axis of the cutter holder, uniformly distributed on a circle, these fingers having a head (14) of a maximum transverse dimension smaller than a minimum diameter of the fixing holes (18), a groove (15) under this head, of a width corresponding to the thickness of the annular part of the cutter, and, under the groove, a minimum transverse dimension larger than a maximum diameter of the fixing holes and, further, at least one locking finger (10) parallel to the fixed fingers (7) and constrained so as to move along an axis parallel to the fixed fingers, angularly offset an approximately identical amount as the fixing holes are from the locking holes on the cutter but with an angular shift preferably in a direction which is the opposite to the direction of rotation of the cutter, so that once the cutter has been engaged over the fixed fingers and engaged in the grooves, in the opposite direction to the direction of rotation of the cutter, introduction of the moving finger into the locking bole locks the cutter in the grooves.

25. The cutter holder as claimed in claim 24, wherein the locking finger (10) has a conical end (16).

26. The cutter holder as claimed in claim 25, wherein the locking finger (10) is cylindrical adjacent its conical end (16) and has a diameter larger than the diameter of the locking hole (19).

27. The cutter holder as claimed in claim 24, wherein the locking finger (10) is mounted on a component (8) mounted to slide on the cutter holder and biased into a locking position by a spring (11).

28. The cutter holder as claimed in claim 25, wherein the locking finger (10) is mounted on a component (8) constrained to axially slide on the cutter holder and is biased into its locking position by a spring (11).

29. The cutter holder as claimed in claim 26, wherein locking finger (10) is mounted on a component (8) mounted to slide on the cutter holder and pushed into its locking position by a spring (11).

30. The cutter holder as claimed in claim 27, wherein the fixed fingers (7) are carried by a flange and the locking finger (10) is guided through this flange.

31. The cutter holder as claimed in claim 28, wherein the fixed fingers (7) are carried by a flange and the locking finger (10) is guided through this flange.

32. The cutter holder as claimed in claim 29, wherein the fixed fingers (7) are carried by a flange and the locking finger (10) is guided through this flange.

33. The cutter holder as claimed in claim 30, wherein the cutter holder has three locking fingers (10) uniformly distributed about the axis of the cutter holder adapted to mate with three locking holes (19) of the cutter, the holes being uniformly distributed about the axis of the cutter holder.

34. The cutter holder as claimed in claim 24, wherein the fingers are located in a circular pattern so as to correspond with the holes of the cutter.

35. The cutter holder as claimed in claim 24, wherein the cutter holder is equipped with a bell housing surrounding the fingers to collect the chips.

36. The cutter holder as claimed in claim 25, wherein the cutter holder is equipped with a bell housing surrounding the fingers to collect the chips.

37. The cutter holder as claimed in claim 26, wherein the cutter holder is equipped with a bell housing surrounding the fingers to collect the chips.

38. The cutter holder as claimed in claim 27, wherein the cutter holder is equipped with a bell housing surrounding the fingers to collect the chips.

39. The cutter holder as claimed in claim 28, wherein the cutter holder is equipped with a bell housing surrounding the fingers to collect the chips.

40. The cutter holder as claimed in claim 29, wherein the cutter holder is equipped with a bell housing surrounding the fingers to collect the chips.

41. The cutter holder as claimed in claim 30, wherein the cutter holder is equipped with a bell housing surrounding the fingers to collect the chips.

42. The cutter holder as claimed in claim 31, wherein the cutter holder is equipped with a bell housing surrounding the fingers to collect the chips.

43. The cutter holder as claimed in claim 32, wherein the cutter bolder is equipped with a bell housing surrounding the fingers to collect the chips.

44. The cutter holder as claimed in claim 33, wherein the cutter holder is equipped with a bell housing surrounding the fingers to collect the chips.

45. The cutter holder as claimed in claim 34, wherein the cutter holder is equipped with a bell housing surrounding the fingers to collect the chips.

46. A cutter holder adapted to securely engage a milling cutter (17) having at least one fixing hole (18) and at least one locking hole (19), the holder having at least one fixed finger (7) constrained to move axially along a rotational axis of the holder, the fixed finger having a groove (15), and a locking finger (10) positioned to move in an axial direction relative to the fixed finger (7) and able to penetrate into the locking hole, said relative axial motion and penetration cause the milling cutter (17) to rotationally engage the groove (15) in a locked manner.

* * * * *

UNITED STATES PATENT AND TRADEMARK OFFICE
CERTIFICATE OF CORRECTION

| | | |
|---|---|---|
| PATENT NO. | : 6,506,000 B2 | Page 1 of 1 |
| APPLICATION NO. | : 09/735829 | |
| DATED | : January 14, 2003 | |
| INVENTOR(S) | : Lechot | |

It is certified that error appears in the above-identified patent and that said Letters Patent is hereby corrected as shown below:

Column 1 after the title on line 1, insert the following header and paragraph:

-- CROSS REFERENCE TO RELATED APPLICATIONS

This application claims priority to Switzerland Application No. 2351/99, filed December 22, 1999. --

Signed and Sealed this
Twenty-third Day of October, 2012

David J. Kappos
*Director of the United States Patent and Trademark Office*